United States Patent [19]

Alburger

[11] 3,992,319
[45] Nov. 16, 1976

[54] INSPECTION PENETRANT PROCESS USING SOLVENCY-INHIBITED REMOVER COMPOSITION

[76] Inventor: James R. Alburger, 5007 Hillard Ave., La Canada, Calif. 91011

[22] Filed: May 14, 1975

[21] Appl. No.: 577,323

Related U.S. Application Data

[63] Continuation-in-part of Ser. No. 327,559, Jan. 29, 1973, abandoned.

[52] U.S. Cl. .................... 252/408; 73/104; 252/301.19
[51] Int. Cl.² ........................... G01N 21/16
[58] Field of Search ............ 252/408, 301.2 P; 73/105, 104

[56] References Cited
UNITED STATES PATENTS

| | | | |
|---|---|---|---|
| 2,405,078 | 7/1946 | Ward | 73/104 |
| 2,953,530 | 9/1960 | Switzer | 252/408 |
| 3,415,112 | 12/1968 | Alburger | 252/408 |
| 3,543,570 | 12/1970 | Mlot-Fijalkowski | 252/408 |
| 3,558,882 | 1/1971 | Mlot-Fijalkowski | 252/408 |
| 3,607,784 | 9/1971 | Mlot-Fijalkowski | 252/408 |
| 3,896,664 | 7/1975 | Alburger | 252/408 |

*Primary Examiner*—Benjamin R. Padgett
*Assistant Examiner*—T. S. Gron

[57] ABSTRACT

A solvent-remover composition and process in which a glycol liquid or water containing an alcohol or glycol-ether accelerator solvent is used as a solvent to remove surface penetrant from test parts in the so-called solvent-remover inspection penetrant process. The remover solvents of the invention provide inhibited solvency for oily water-insoluble dyed penetrant liquids, thus preventing excessively rapid depletion of entrapments in surface cracks. The flaw detection capability of the solvent-remover penetrant process is thereby improved.

2 Claims, No Drawings

INSPECTION PENETRANT PROCESS USING SOLVENCY-INHIBITED REMOVER COMPOSITION

This application is a continuation-in-part of my co-pending application Ser. No. 327,559, filed Jan. 29, 1973, now abandoned, for "Inspection Penetrant Process Using Solvency-Inhibited Remover Composition."

The invention relates to inspection penetrant materials and processes. More particularly, the invention relates to an improvement in the so-called solvent-remover process in which surface penetrant is removed from test parts by cleaning with a liquid which is solvent for the dyed penetrant.

The well-known solvent-remover method of inspection penetrant usage employs a visible-color or fluorescent penetrant which is applied to test surfaces by dipping, brushing, or spraying. The dyed penetrant is allowed to dwell on the test surface for a period of time, during which it enters any surface flaws which are present. Then, excess surface penetrant is removed by flushing the test surface with a remover liquid, or by wiping the test surface with a cloth or sponge moistened with a remover liquid which is solvent for the penetrant liquid.

Application of a solvent remover, as described above, is intended to remove only excess surface penetrant, leaving entrapments of penetrant in any cracks or other flaws which may be present. Once the surface penetrant has been removed, providing a relatively clean background on the test surface, entrapments of dyed penetrant which remain in surface flaws may be observed, visually or photoelectrically, by the dye indicator which is present in the penetrant.

The conventional solvent remover inspection penetrant process usually entails a step of development of indications following the step of remover application. In this step of development, a thin coating of powder particles is applied to the test surface, a preferred developer composition being a suspension of powder particles in a carrier liquid such as alcohol.

The developer acts to draw out and absorb entrapments of penetrant from surface cracks. In some cases, the process is carried out without using a developer, in which case the entrapments of penetrant are viewed as they exist in surface flaws, or as they exude from the flaws. This mode of parts treatment is known as "self-development."

In any event, the effectiveness of the solvent-remover inspection penetrant process in providing useful indications of crack defects depends largely on the efficiency to which entrapments of penetrant are retained in the cracks throughout the step of application of the remover solvent. The normally employed technique of solvent remover application is one in which the cloth moistened with the solvent is squeezed almost dry, so that very little solvent liquid is applied to the test surface. Also, the number of wiping strokes on the test surface is held to a minimum, so as to avoid stripping out entrapments of penetrant to an excessive degree.

In the past, it has been the practice to employ as the solvent remover, a liquid such as mineral thinner, kerosene, alcohol, or any one of a variety of chlorinated hydrocarbon liquids, such as 1.1.1-trichloroethane, perchloroethylene, and the like. The conventional solvent remover liquids appear to have been chosen for their ability to quickly provide a relatively clean test surface with a minimum background of residues of dyed penetrant. I have discovered that existing solvent removers suffer from a serious drawback, in that they are characterized by an excessive degree of mobility and solvency, such that in addition to removing surface penetrant, entrapments of penetrant in surface cracks are also removed to an excessive degree. This excessive degree of solvent remover activity acts to destroy many desired flaw indications, particularly indications of small, shallow crack defects.

I have devised a technique for measuring the rate at which flaw indications are depleted by solvent action, washing, or emulsification, as applicable, and I have found it possible to assign values of "Indication Depletion Time Constants" to various materials such as water-washable penetrants, emulsifiers and solvent removers. In essence, my method of evaluation involves the measurement by photoelectric means, of the loss of brightness of a pattern of indications during the course of remover application. The method yields, for each material or combination of materials, a time constant which is a measure of the time in seconds of remover contact required to deplete the color or fluorescent brightness of an indication to 50% of its initial value. Measurements in this regard are made using a "standard" craze-crack test panel having a pattern of closely spaced cracks of known depth and width.

The significance of the Indication Depletion Time Constant is that in cases where processing conditions require a prolonged contact of the remover with the test surface, the Indication Depletion Time Constant must be large, otherwise indications may be lost. By using the methods which I have devised, and which have become standard procedures under Air Force MIL-Specifications and Industrial Specifications, I have been able to assign Indication Depletion Time Constants to penetrant process materials, and have thus been able to assign ratings of relative indication stability for such materials. It turns out that Indication Depletion Time Constants for typical solvent-removable penetrants and solvent removers (using a cracked anodic test panel for evaluation) fall in the range of from a fraction of a second to only a few seconds, and such time constant values are so small that it becomes quite difficult or even impossible to accurately control the flaw detection performance characteristic of the solvent-remover inspection penetrant process.

There are numerous cases where it is necessary to obtain a considerably higher degree of indication stability, as might be provided by a penetrant and remover combination having an Indication Depletion Time Constant in the range of from about 10 seconds up to as much as 2000 seconds. One such inspection application is the study of inter-crystalline separations in plated surfaces, or ceramics. Another application is the testing of molybdenum disilicide heat resistant coatings for the presence of irregularities and discontinuities. In any of these applications, and others, which require extremely high flaw detection sensitivity combined with an extremely high degree of indication stability, it is essential that the penetrant/remover combination shall exhibit an enhanced stability of flaw entrapments or indications, as compared with existing solvent-remover process materials.

The principal object of the invention, therefore, is to provide a solvency-inhibited remover composition for use in the inspection penetrant process.

Another object of the invention is to provide a method of adjusting and controlling the Indication Depletion Time Constant value of a solvent-remover inspection penetrant to a point within the approximate range of from about 10 seconds up to about 2000 seconds.

These and other objects of the invention will in part be obvious and will in part become apparent from the following description thereof.

I have discovered a family of solvent liquids and liquid compositions which satisfy the requirement of high values of Indication Depletion Time Constant, these materials consisting of liquid glycols, water-diluted liquid glycols, and water-diluted liquid glycol-ethers. Among the various liquid glycols which are useful as solvency-inhibited removers for inspection penetrants are the following:

Ethylene glycol,
Diethylene glycol,
Triethylene glycol,
Tetraethylene glycol,
Propylene glycol,
Dipropylene glycol,
Hexylene glycol,
1,5-Pentanediol
Glycerine,
1,2,6-Hexanetriol,
Polyethylene glycol (Mol. wt. — 200 to 1000), and
Polypropylene glycol (Mol. wt. — 200 to 450).

In the above listing, certain of the polyethylene glycols have melting points at or slightly above room temperature. Such materials are suitable for use on hot test parts where the elevated temperature of the test piece keeps the glycol in a fluid condition. For the purpose of this specification, certain of the triols, such as glycerine (glycerol), are considered to be in the family of glycols.

I have found that the poly-glycols and certain of the triols exhibit less solvency than the lower molecular weight materials. I have also found that specific desired values of Indication Depletion Time Constants may be obtained by preparing appropriate mixtures of materials so as to provide a desired intermediate value of the time constant.

My improved solvent remover inspection penetrant process is carried out as follows: Test parts to be inspected for the presence of surface cracks are first treated with a dyed penetrant, which may be visible color such as red, or fluorescent. After a suitable dwell time, during which the penetrant enters any surface flaws which are present, the test surface is drained, wiped, or washed with water so as to remove the bulk of adhering penetrant. A glycol selected from the foregoing listing is then applied to the test surface, a preferred method being by spraying the glycol liquid onto the part, although the glycol liquid may be applied by brushing or dipping, or even by soaking a cloth in the liquid glycol and wiping the test surface with the moistened cloth. After the test surface is thoroughly wetted with the glycol remover, the surface is wiped clean with a clean absorbent cloth, or the surface may be washed clean with a spray of water. The solvent action of the glycol remover with respect to the penetrant is slow enough so that there is ample time for applying and removing the glycol from the test surface without stripping out entrapments from shallow surface flaws.

While entirely satisfactory remover action may be achieved by use of the above-described glycol liquids, or mixtures of same, I have found that in many cases the addition of a small amount of wetting agent (i.e., a nonionic water-soluble surfactant) to the glycol liquid serves to improve the ability of the glycol remover to wet the test surface uniformly. For this purpose, only a small percentage of wetting agent is needed to provide a suitable wetting action. Concentrations of wetting agent ranging from as little as 0.1% up to as much as 20% may be utilized. Of course, in many cases, no wetting agent is needed.

I have also found that under certain special conditions of usage, to be described hereinafter, water may be used as a solvent remover for the oily water-insoluble dyed penetrants employed in the solvent-remover process. Heretofore, water has been used as a remover only for the so-called water-washable inspection penetrants, i.e., those penetrants which contain a detergent ingredient which renders the penetrant self-emulsifiable. Also, water is commonly used as a final wash rinse in the so-called post-emulsifier process. However, water has not been used in the past, and has been contra-indicated for use with water-insoluble penetrants as a remover to reveal flaw indications.

Water has been used in the past, in the form of a high pressure spray, for the purpose of stripping off and recovering excess water-insoluble penetrant from test surfaces prior to application of an emulsifier in the post-emulsifier process, or even prior to the application of a solvent remover in the solvent-remover process. This usage of water is not effective in removing surface penetrant to reveal flaw indications, and hence such usage falls outside the scope of the present invention.

Water, alone, is normally nonsolvent for the oily water-insoluble dyed penetrants which are employed in the solvent-remover process. At least, the solvency of water is extremely small, so that any Indication Depletion Time Constant which might exist is so large that for all practical purposes no depletion of indications occurs at all upon the application of plain water to penetrant-treated test surfaces. Thus, surfaces treated with oily, water-insoluble inspection penetrants cannot be cleaned properly by use of water alone so as to reveal flaw indications.

I have discovered that the Indication Depletion Time Constant characteristic of any of the glycols, and even of water, can be adjusted and controlled to a desired value by the addition of a suitable accelerator agent or solvent-coupler which may enhance the solvency capability of the glycol or water. Solvency enhancing agents may be selected from the group consisting of water-soluble alcohols and glycol ethers.

Any water-soluble alcohol or glycol ether may be utilized for the purpose of accelerating the solvency of a glycol or water so as to provide a desired Indication Depletion Time Constant. I have found that any alcohol or glycol ether may be added to water (or glycol) to a concentration of from about 5% to 75%, with the result that Indication Depletion Time Constants in the range of from about 10 to 2000 seconds may be obtained.

It will be understood that any one or a combination of the above-identified glycol liquids may be combined with water, with or without the presence of an accelerator solvent, so as to provide a remover composition having an Indication Depletion Time Constant characteristic falling within the desired range of from about 10 to 2000 seconds.

It will also be understood that water may be used as a solvent remover, provided that a glycol ether or an alcohol accelerator or solvent-coupler is included with the water in an amount sufficient to reduce the Indication Depletion Time Constant to a value below about 2000 seconds down to about 10 seconds. This result may be obtained by utilizing a glycol ether or alcohol solvent coupler in water at a concentration of from about 5 up to 75%. For the purpose of this specification, water-soluble alcohols and glycol ethers are included together under the generic designation "solvent-coupler". Suitable solvent-couplers for use in the compositions of the invention include the following:

Methanol,
Ethanol,
Butanol,
Isopropanol,
1-Propanol,
2-Butanol,
Ethylene glycol monomethyl ether,
Ethylene glycol monoethyl ether,
Ethylene glycol monobutyl ether,
Ethylene glycol dibutyl ether,
Diethylene glycol monomethyl ether,
Diethylene glycol monoethyl ether,
Diethylene glycol monobutyl ether,
Diethylene glycol dibutyl ether,
Butoxytriglycol,
Methoxytriglycol,
Ethoxytriglycol, and
1-Butoxyethoxy-2-propanol.

The following examples are indicative of the Indication Depletion Time Constants which are obtainable with the remover materials and compositions of the invention.

EXAMPLE I

Diethylene glycol, used alone, provides a Time Constant of about 15 seconds to 20 seconds.

EXAMPLE II

Diethylene glycol, diluted with equal parts of water, provides a Time Constant of about 150 seconds.

EXAMPLE III

A mixture of 50 parts water and 25 parts isopropanol provides a Time Constant of about 60 seconds.

EXAMPLE IV

A mixture of equal parts water and isopropanol provides a Time Constant of about 20 seconds.

EXAMPLE V

A mixture of 25 parts water, 25 parts isopropanol, and 25 parts diethylene glycol provides a Time Constant of about 25 seconds.

EXAMPLE VI

A mixture of equal parts water and ethylene glycol monoethyl ether provides a Time Constant of about 30 seconds.

EXAMPLE VII

A mixture of one part diethylene glycol monobutyl ether and three parts water provides a Time Constant of about 40 seconds.

EXAMPLE VIII

Glycerin, used alone, provides a Time Constant greater than 500 seconds.

EXAMPLE IX

Triethylene glycol, used alone, provides a Time Constant of about 16 seconds.

EXAMPLE X

Polyethylene glycol (M.W. — 200), used alone, provides a Time Constant of about 15 seconds.

Any of the above or equivalent mixtures may be diluted or further diluted with water so as to provide larger values of Time Constants. For practical use conditions, the preferred range of Depletion Time Constant values is from about 15 to 100 seconds, although values ranging from about 10 seconds up to as much as 2000 seconds might be found useful. Time constant values greater than about 2000 seconds have little utility due to the excessively long time which is required to achieve a satisfactory cleaning of test surfaces.

It will be understood that the above-identified glycols may be used singly, selectively, and in combination, or they may be diluted with water up to as much as five or six parts water to one part glycol, whereby an Indication Depletion Time Constant may be obtained which falls within the desired range of from 10 to 2000 seconds. It will also be understood that a solvent-coupler may be included in the remover formulation along with the glycol, up to as much as 50%. Finally, it will be understood that a small amount of wetting agent, up to as much as 20% may be included in the glycol-type remover formulations. A representative remover composition of the glycol type may, therefore, be expressed by the following formulation, stated in weight percentages:

EXAMPLE XI

| Glycol | 15% | to | 100% |
| Water | zero | to | 85% |
| Solvent coupler | zero | to | 75% |
| Wetting agent | zero | to | 20% |

A representative remover composition of the invention of the water/solvent-coupler type may, therefore, be expressed by the following formulation, stated in weight percentages:

EXAMPLE XII

| Solvent-coupler (alcohol or glycol-ether) | 5% | to | 75% |
| Water | 25% | to | 95% |

A remover composition of the Example XII type may be thought of as an accelerated water-wash composition, or conversely as a solvency-inhibited solvent-remover or solvent-coupler composition. I prefer to designate such compositions as "solvency-inhibited solvent-coupler removers." With regard to the compositions of the Example XI type, I prefer to designate such compositions a "solvency-inhibited solvent removers".

As pointed out above, any of the remover compositions of the invention may be employed in the so-called hand-wipe mode of usage or the dip-tank mode of usage, depending on the preference of the user. In general, it is found preferable to employ the Example XI type compositions in the hand-wipe mode of usage, while the Example XII type compositions are best utilized in a dip-tank mode of usage.

In the dip-tank mode of usage, test surfaces are first treated with the oily water-insoluble dyed penetrant. The test surfaces are usually preconditioned under a spray of plain water which acts to strip off the bulk of the penetrant liquid. This stripped-off penetrant may be returned to a reservoir where it floats to the surface of the water, being collected for re-use. After pre-conditioning, the test parts may be immersed and mildly agitated in a tank containing the remover composition (of the Example XII type), or the remover may be applied to test surfaces by spray or by a flow of liquid to provide a copious flushing action. The used remover liquid is drained back into a tank or reservoir from which it is re-used. Finally, after a suitable dwell time in contact with the remover composition, the test surfaces are rinsed with plain water, dried, and inspected for the presence of flaw entrapment indications.

The Example XII type compositions and their preferred mode of usage are similar in certain respects to conventional emulsifier-type removers, except that they contain no surfactant ingredients. This is an important distinction, since I have discovered that one of the major drawbacks of the conventional emulsifier-type removers is that they contain surface-active constituents, and although these constituents serve to promote emulsification wash removal of the oily penetrant from test surfaces, they also create a problem known as "adsorption background noise." Thus, water-washable (self-emulsifiable) penetrants and emulsifiers which contain detergents all tend to cause indicator dyes (particularly fluorescent dyes) to become adsorbed into or on certain types of porous surfaces such as anodized aluminum or surfaces having heat resistant coatings. The mass of background indications which are produced by this adsorption of dyes can and often does interfere with and obscure actual crack indications. I have discovered that those compositions of the invention which contain no surfactants (or wetting agents) do not suffer from the effects of unwanted adsorption background "noise."

Another difficulty which is inherent in removers of the emulsifier type is that the detergent ingredient which is found in such emulsifiers acts to form oil-water emulsions, and the emulsifier constituents are not easily separated and recovered from the wash water for re-cycling and re-use. Compositions of the Example XII type are easily recoverable for re-use, since the glycol ether material is easily extracted from the final rinse water simply by bubbling the rinse water through a column of solvent such as perchloroethylene in accordance with the teachings of my copending appln. Ser. No. 432,752, filed Jan. 11, 1974, now U.S. Pat. No. 3,926,044, for "A Closed-Loop Water-Washable Inspection Penetrant Process."

Accordingly, the compositions of the Example XII type present distinct advantages over conventional emulsifiers or diluted emulsifiers of the so-called "hydrophilic" type, in that they exhibit a minimum amount of background adsorption noise, and their chemical elements are easily recovered for re-use. With regard to the compositions of the Example XI type, certain of these present distinct advantages over conventional solvent removers, in that they may be utilized on hot test surfaces such as weldments. For example, polypropylene glycol having a molecular weight in the range of 400 may be used on hot parts at temperatures up to 300° F. or more.

In all cases, the compositions of Examples XI and XII provide significant advantages over conventional solvent removers or emulsifier-type removers, in that they yield enhanced stability of flaw indications.

Although the invention has been described with reference to particular embodiments thereof, it will be understood that various changes and modifications may be made therein without departing from the spirit of the invention nor the scope of the appended claims.

I claim:

1. In a solvent-remover inspection penetrant process in which a solvent-soluble, water-insoluble dyed liquid penetrant is applied to test parts, surface penetrant is removed by applying a solvent remover to said parts, and said parts are inspected for residual entrapments of penetrant liquid in surface flaws, the improvement wherein said solvent remover consists essentially of the following formulation, stated in weight percentages:

| | | | |
|---|---|---|---|
| Glycol | 15% | to | 100% |
| Water | zero | to | 85% |
| Solvent-coupler | zero | to | 75% |
| Wetting agent | zero | to | 20% | said glycol being at least one member selected from the group consisting of

Ethylene glycol,
Diethylene glycol,
Triethylene glycol,
Tetraethylene glycol,
Propylene glycol,
Dipropylene glycol,
Hexylene glycol,
1,5-Pentanediol,
Glycerin,
1,2,6-Hexanetriol,
Polyethylene glycol (Mol. wt. — 200 to 1000), and
Polypropylene glycol (Mol. wt. — 200 to 450).

2. In a solvent-remover inspection penetrant process in which a solvent-soluble, water-insoluble dyed penetrant liquid is applied to test parts, surface penetrant is removed by applying a solvent remover to said parts, and said parts are inspected for residual entrapments of penetrant liquid in surface flaws, the improvement wherein said solvent remover consists essentially of the following formulation, stated in weight percentages:

| | | | |
|---|---|---|---|
| Solvent-coupler | 5% | to | 75% |
| Water | 25% | to | 95% | said solvent-coupler being at least one member selected from the group consisting of Methanol,
Ethanol,
Butanol,
Isopropanol,
1-Propanol,
2-Butanol, Ethylene glycol monomethyl ether,
Ethylene glycol monoethyl ether,
Ethylene glycol monobutyl ether,
Ethylene glycol dibutyl ether,
Diethylene glycol monomethyl ether,
Diethylene glycol monoethyl ether,
Diethylene glycol monobutyl ether,
Diethylene glycol dibutyl ether,
Butoxytriglycol,
Methoxytriglycol,
Ethoxytriglycol, and,
1-Butoxyethoxy-2-propanol.

* * * * *